United States Patent
Johnson

(10) Patent No.: US 11,547,392 B2
(45) Date of Patent: Jan. 10, 2023

(54) METHOD OF COLLECTING AND PRESERVING A BIOLOGICAL SAMPLE

(71) Applicant: SPECTRUM SOLUTIONS, LLC, Draper, UT (US)

(72) Inventor: Neil Jeremy Johnson, Riverton, UT (US)

(73) Assignee: Spectrum Solutions L.L.C., Draper, UT (US)

( * ) Notice: Subject to any disclaimer, the term of this patent is extended or adjusted under 35 U.S.C. 154(b) by 0 days.

(21) Appl. No.: 17/178,918

(22) Filed: Feb. 18, 2021

(65) Prior Publication Data

US 2021/0177385 A1    Jun. 17, 2021

Related U.S. Application Data

(60) Division of application No. 17/093,815, filed on Nov. 10, 2020, now Pat. No. 11,284,867, which is a
(Continued)

(51) Int. Cl.
*A61B 10/02* (2006.01)
*B01L 3/00* (2006.01)

(52) U.S. Cl.
CPC .......... *A61B 10/02* (2013.01); *B01L 3/50825* (2013.01); *B01L 3/523* (2013.01);
(Continued)

(58) Field of Classification Search
CPC ..... A61B 10/02; B01L 3/50825; B01L 3/523; B01L 2200/0689; B01L 2200/10;
(Continued)

(56) References Cited

U.S. PATENT DOCUMENTS 2,275,567 A    11/1933  Smith
2,631,521 A    11/1949  Atkins, Jr.
(Continued)

FOREIGN PATENT DOCUMENTS

AU    2013206564      7/2013
CA      2072331 C   12/1992
(Continued)

OTHER PUBLICATIONS

International Search Report and Written Opinion issued in PCT/US 19/62484 dated Jan. 29, 2020.
(Continued)

*Primary Examiner* — Benjamin R Whatley
*Assistant Examiner* — Jacqueline Brazin
(74) *Attorney, Agent, or Firm* — Workman Nydegger

(57) ABSTRACT

A biological sample collection system can include (i) a sample collection vessel having an opening for receiving a biological sample, (ii) a selectively movable valve comprising a core and a collar disposed about the core, and (iii) a sealing cap coupled to the collar and comprising a reagent chamber for storing a measure of sample preservation reagent. The sealing cap is configured to associate—and form a fluid tight connection—with the sample collection vessel such that associating the sealing cap with the sample collection vessel causes a physical rearrangement of the core relative to the collar such that a fluid vent associated with the core is moved into fluid communication with the reagent chamber, thereby permitting sample preservation reagent to pass from the regent chamber to the sample collection vessel.

18 Claims, 3 Drawing Sheets

Related U.S. Application Data continuation of application No. 16/906,830, filed on Jun. 19, 2020.

(60) Provisional application No. 62/864,500, filed on Jun. 20, 2019.

(52) U.S. Cl.
CPC ... *B01L 2200/0689* (2013.01); *B01L 2200/10* (2013.01); *B01L 2200/16* (2013.01); *B01L 2300/042* (2013.01); *B01L 2300/047* (2013.01); *B01L 2300/049* (2013.01); *B01L 2300/0832* (2013.01)

(58) Field of Classification Search
CPC ........... B01L 2200/16; B01L 2300/042; B01L 2300/047; B01L 2300/049; B01L 2300/0832
USPC ....................................................... 600/562
See application file for complete search history.

(56) References Cited

U.S. PATENT DOCUMENTS

| | | |
|---|---|---|
| 2,653,611 A | 11/1950 | Smith |
| 2,773,591 A | 10/1953 | Jensen |
| 2,764,983 A | 10/1956 | Barasch et al. |
| 3,321,097 A | 5/1967 | Solowey |
| 3,340,873 A | 9/1967 | Solowey |
| 3,347,410 A | 10/1967 | Schwartzman |
| 3,441,179 A | 4/1969 | Ragan |
| 3,464,414 A | 9/1969 | Sponnoble |
| 3,518,164 A | 6/1970 | Andelin et al. |
| 3,536,191 A | 10/1970 | Williams |
| 3,537,606 A | 11/1970 | Solowey |
| 3,603,484 A | 9/1971 | Ogle |
| 3,651,990 A | 3/1972 | Cernei |
| 3,670,914 A | 6/1972 | Poulsen, Jr. |
| 3,674,028 A | 7/1972 | Ogle |
| 3,684,455 A | 8/1972 | Vacirca et al. |
| 3,731,853 A | 5/1973 | Baumann et al. |
| 3,792,699 A | 2/1974 | Tobin et al. |
| 3,846,077 A | 11/1974 | Ohringer |
| 3,878,571 A | 4/1975 | Seeley |
| 3,924,741 A | 12/1975 | Kachur et al. |
| 3,968,872 A | 7/1976 | Cavazza |
| 4,102,451 A | 7/1978 | Clarke et al. |
| 4,150,950 A | 4/1979 | Takeguchi et al. |
| 4,195,730 A | 4/1980 | Hunt |
| 4,221,291 A | 9/1980 | Hunt |
| 4,311,792 A | 1/1982 | Avery |
| 4,324,859 A | 4/1982 | Saxholm |
| 4,418,702 A | 12/1983 | Brown et al. |
| 4,465,183 A | 8/1984 | Saito et al. |
| 4,473,530 A | 9/1984 | Villa-Real |
| 4,589,548 A | 5/1986 | Fay |
| 4,591,050 A | 5/1986 | Finke et al. |
| 4,615,437 A | 10/1986 | Finke et al. |
| 4,634,003 A | 1/1987 | Ueda et al. |
| 4,727,985 A | 3/1988 | McNeirney et al. |
| 4,741,346 A | 5/1988 | Wong et al. |
| 4,761,379 A | 8/1988 | Williams et al. |
| 4,920,975 A | 5/1990 | Fay |
| 4,932,081 A | 6/1990 | Burns |
| 4,982,875 A | 1/1991 | Pozzi et al. |
| 5,029,718 A | 7/1991 | Rizzardi |
| 5,119,830 A | 6/1992 | Davis |
| 5,128,104 A | 7/1992 | Murphy et al. |
| 5,152,965 A | 10/1992 | Fisk et al. |
| 5,266,266 A | 11/1993 | Nason |
| 5,268,148 A | 12/1993 | Seymour |
| 5,291,991 A | 3/1994 | Meyer |
| 5,330,048 A | 7/1994 | Haber et al. |
| 5,335,673 A | 8/1994 | Goldstein et al. |
| 5,422,241 A | 6/1995 | Goldrick et al. |
| 5,425,921 A | 6/1995 | Coakley et al. |
| 5,445,965 A | 8/1995 | Stone |
| 5,478,722 A | 12/1995 | Caldwell |
| 5,490,971 A | 2/1996 | Gifford et al. |
| 5,494,646 A | 2/1996 | Seymour |
| 5,643,767 A | 7/1997 | Fischetti et al. |
| 5,658,531 A | 8/1997 | Cope et al. |
| 5,714,380 A | 2/1998 | Neri et al. |
| 5,786,228 A | 7/1998 | Charlton |
| 5,827,675 A | 10/1998 | Skiffington et al. |
| 5,869,328 A | 2/1999 | Antoci et al. |
| 5,921,396 A | 7/1999 | Brown, Jr. |
| 5,927,549 A | 7/1999 | Wood |
| 5,935,864 A | 8/1999 | Schramm et al. |
| 5,941,380 A | 8/1999 | Rothman |
| 5,950,819 A | 9/1999 | Sellars |
| 5,967,309 A | 10/1999 | Robles-Gonzalez et al. |
| 5,968,746 A | 10/1999 | Schneider |
| 5,973,137 A | 10/1999 | Heath |
| 5,976,829 A | 11/1999 | Birnboim |
| 5,984,141 A | 11/1999 | Gibler |
| 6,003,728 A | 12/1999 | Elliott |
| 6,113,257 A | 9/2000 | Sharon et al. |
| 6,121,055 A | 9/2000 | Hargreaves |
| 6,138,821 A | 10/2000 | Hsu |
| 6,148,996 A | 11/2000 | Morini |
| 6,149,866 A | 11/2000 | Luotola et al. |
| 6,204,375 B1 | 3/2001 | Lader |
| 6,224,922 B1 | 5/2001 | Fonte |
| 6,228,323 B1 | 5/2001 | Asgharian et al. |
| 6,277,646 B1 | 8/2001 | Guirguis et al. |
| 6,309,827 B1 | 10/2001 | Goldstein et al. |
| 6,503,716 B1 | 1/2003 | Lai et al. |
| 6,524,530 B1 | 2/2003 | Igarashi et al. |
| 6,527,110 B2 | 3/2003 | Moscovitz |
| 6,528,641 B2 | 3/2003 | Lader |
| 6,533,113 B2 | 3/2003 | Moscovitz |
| 6,617,170 B2 | 9/2003 | Augello et al. |
| 6,776,959 B1 | 8/2004 | Helftenbein |
| 7,282,371 B2 | 10/2007 | Helftenbein |
| 7,464,811 B2 | 12/2008 | Patterson et al. |
| 7,482,116 B2 | 1/2009 | Birnboim |
| 7,748,550 B2 | 7/2010 | Cho |
| 8,084,443 B2 | 12/2011 | Fischer et al. |
| 8,137,958 B2 | 3/2012 | Grimes et al. |
| 8,293,467 B2 | 10/2012 | Fischer et al. |
| 8,415,330 B2 | 4/2013 | Fischer et al. |
| 8,418,865 B2 | 4/2013 | Cho |
| 8,669,240 B2 | 3/2014 | Fischer et al. |
| 8,728,414 B2 | 5/2014 | Beach et al. |
| 9,079,181 B2 | 7/2015 | Curry et al. |
| 9,138,747 B2 | 9/2015 | Williams et al. |
| 9,212,399 B2 | 12/2015 | Fischer et al. |
| 9,370,775 B2 | 6/2016 | Harvey et al. |
| 9,442,046 B2 | 9/2016 | Biadillah et al. |
| 9,523,115 B2 | 12/2016 | Birnboim |
| 9,683,256 B2 | 6/2017 | Fischer et al. |
| 9,732,376 B2 | 8/2017 | Oyler et al. |
| 10,000,795 B2 | 6/2018 | Birnboim et al. |
| 10,174,362 B2 | 1/2019 | Gaeta |
| 10,189,020 B2 | 1/2019 | Williams et al. |
| 10,525,473 B2 | 1/2020 | Williams |
| 10,576,468 B2 | 3/2020 | Biadillah et al. |
| 10,619,187 B2 | 4/2020 | Birnboim |
| 10,767,215 B2 | 9/2020 | Birnboim et al. |
| 10,774,368 B2 | 9/2020 | Gaeta |
| 11,002,646 B2 | 5/2021 | Biadillah et al. |
| 2001/0023072 A1 | 9/2001 | Crawford et al. |
| 2001/0031473 A1 | 10/2001 | Dattagupta et al. |
| 2002/0110810 A1 | 8/2002 | Shuber |
| 2002/0197631 A1 | 12/2002 | Lawrence et al. |
| 2003/0114430 A1 | 6/2003 | MacLeod et al. |
| 2003/0132244 A1 | 7/2003 | Birkmayer et al. |
| 2003/0143752 A1 | 7/2003 | Feldsine et al. |
| 2004/0014237 A1 | 1/2004 | Sugiyama et al. |
| 2004/0038269 A1 | 2/2004 | Birnboim |
| 2004/0038424 A1 | 2/2004 | Maples |
| 2004/0101859 A1 | 5/2004 | Moon et al. |
| 2004/0161788 A1 | 8/2004 | Chen et al. |

(56) References Cited

U.S. PATENT DOCUMENTS

| | | |
|---|---|---|
| 2004/0200740 A1 | 10/2004 | Cho |
| 2004/0200741 A1 | 10/2004 | Cho |
| 2004/0237674 A1 | 12/2004 | Wu et al. |
| 2005/0079484 A1 | 4/2005 | Heineman et al. |
| 2005/0101920 A1* | 5/2005 | Keane ............. A61B 5/150213 604/218 |
| 2005/0112024 A1 | 5/2005 | Guo et al. |
| 2005/0123928 A1 | 6/2005 | Das et al. |
| 2006/0216196 A1 | 9/2006 | Satoh et al. |
| 2006/0245977 A1 | 11/2006 | Bodner |
| 2006/0260959 A1 | 11/2006 | Patterson et al. |
| 2007/0072229 A1 | 3/2007 | Bialozynski et al. |
| 2007/0134134 A1 | 6/2007 | Watts et al. |
| 2007/0202511 A1 | 8/2007 | Chen et al. |
| 2007/0280042 A1 | 12/2007 | Yamanaka |
| 2007/0287149 A1 | 12/2007 | Shomi et al. |
| 2008/0003574 A1 | 1/2008 | Michalik et al. |
| 2008/0067084 A1* | 3/2008 | Patterson ........... B65D 51/2892 206/219 |
| 2008/0156674 A1 | 7/2008 | Correale et al. |
| 2008/0187924 A1 | 8/2008 | Korfhage et al. |
| 2008/0194986 A1 | 8/2008 | Conway et al. |
| 2008/0226506 A1 | 9/2008 | Ohashi |
| 2008/0260581 A1 | 10/2008 | Rosman et al. |
| 2008/0293156 A1 | 11/2008 | Smith |
| 2009/0022631 A1 | 1/2009 | Ohashi et al. |
| 2009/0023219 A1 | 1/2009 | Perez |
| 2009/0133366 A1* | 5/2009 | Cronin ............... B65D 51/2892 53/420 |
| 2009/0216213 A1 | 8/2009 | Muir et al. |
| 2009/0312285 A1 | 12/2009 | Fischer et al. |
| 2011/0068102 A1 | 3/2011 | Porter |
| 2011/0212002 A1 | 9/2011 | Curry et al. |
| 2012/0046574 A1 | 2/2012 | Skakoon |
| 2012/0220043 A1 | 8/2012 | Sangha |
| 2012/0308448 A1 | 12/2012 | Wong |
| 2012/0325721 A1 | 12/2012 | Plante et al. |
| 2013/0011311 A1 | 1/2013 | Kim |
| 2013/0026691 A1 | 1/2013 | Cahill et al. |
| 2013/0209993 A1 | 8/2013 | Aronowitz |
| 2013/0248045 A1 | 9/2013 | Williams et al. |
| 2014/0051178 A1 | 2/2014 | Niggel et al. |
| 2014/0120531 A1 | 5/2014 | Biadillah et al. |
| 2015/0056716 A1* | 2/2015 | Oyler .................... C12Q 1/6806 436/176 |
| 2015/0140681 A1 | 5/2015 | Meng et al. |
| 2015/0190122 A1 | 7/2015 | Butlin et al. |
| 2015/0203258 A1 | 7/2015 | Staton |
| 2015/0289856 A1 | 10/2015 | Saqi et al. |
| 2015/0343438 A1 | 12/2015 | Williams et al. |
| 2016/0023210 A1 | 1/2016 | Birkner et al. |
| 2016/0045187 A1 | 2/2016 | Terbrueggen et al. |
| 2016/0296936 A1 | 10/2016 | Trump et al. |
| 2017/0001191 A1 | 1/2017 | Biadillah et al. |
| 2017/0350797 A1 | 12/2017 | Estep et al. |
| 2018/0344568 A1 | 12/2018 | Phillips et al. |
| 2019/0151842 A1 | 5/2019 | Williams et al. |
| 2019/0200966 A1 | 7/2019 | Zhan et al. |
| 2020/0156056 A1 | 5/2020 | Williams et al. |
| 2020/0254460 A1 | 8/2020 | Blair et al. |
| 2020/0269232 A1 | 8/2020 | Williams et al. |
| 2020/0284704 A1 | 9/2020 | Biadillah et al. |

FOREIGN PATENT DOCUMENTS

| | | |
|---|---|---|
| CA | 2236240 C | 10/1999 |
| CA | 2348152 A1 | 2/2000 |
| CA | 2488769 C | 12/2003 |
| DE | 10219117 C1 | 10/2003 |
| EP | 0215533 A2 | 3/1987 |
| EP | 0215735 A1 | 3/1987 |
| EP | 0734684 A1 | 10/1996 |
| EP | 0586024 B1 | 1/1999 |
| EP | 1513952 B1 | 3/2005 |
| GB | 1403274 A | 8/1975 |
| JP | H05187976 A | 7/1993 |
| JP | H06046856 A | 2/1994 |
| JP | H09509495 A | 9/1997 |
| JP | H10273161 A | 10/1998 |
| JP | 2000346838 A | 12/2000 |
| WO | WO8906704 A1 | 7/1989 |
| WO | WO1991002740 | 3/1991 |
| WO | WO9705248 A2 | 2/1997 |
| WO | WO1997048492 A1 | 12/1997 |
| WO | WO9803265 | 1/1998 |
| WO | WO1998004899 A1 | 2/1998 |
| WO | WO98038917 | 9/1998 |
| WO | WO1998044158 A1 | 10/1998 |
| WO | WO9929904 | 6/1999 |
| WO | WO0006780 A1 | 2/2000 |
| WO | WO2000010884 A1 | 3/2000 |
| WO | WO200077235 | 12/2000 |
| WO | WO0134844 A1 | 5/2001 |
| WO | WO2002088296 A1 | 11/2002 |
| WO | WO2003/104251 A2 | 12/2003 |
| WO | 2004/017895 A2 | 3/2004 |
| WO | WO2004094635 A1 | 11/2004 |
| WO | WO 2004104181 | 12/2004 |
| WO | WO2005051775 A2 | 6/2005 |
| WO | WO2005111210 A1 | 11/2005 |
| WO | 2005/120977 A1 | 12/2005 |
| WO | WO2006096973 A1 | 9/2006 |
| WO | 2012/177656 A2 | 12/2012 |

OTHER PUBLICATIONS

International Search Report and Written Opinion received for PCT Patent Application No. PCT/US20/038858, dated Sep. 30, 2020, 11 pages.

International Search Report issued in PCT/US2018/030681 dated Jul. 12, 2018.

Vintiloiu et al., "Effect of ethylenediaminetetraacetic acid (EDTA) on the bioavailability of trace elements during anaerobic digestion" Chemical Engineering Journal, vol. 223, May 1, 2013, pp. 436-441.

Muelenbelt et al., "High-Yield Noninvasive Human Genomic DNA Isolation Method for Genetic Studies in Geographically Dispersed Families and Populations" 1995.

Seutin et al., "Preservation of avian blood and tissue samples for DNA analyses" 1990.

Doosti et al., "Study of the frequency of Clostridium difficile tcdA, tcdB, cdtA and cdtB genes in feces of Calves in south west of Iran" Ann Clin Microbiol Antimicrob. Jun. 5, 2014.

Longmire et al., "Use of "Lysis Buffer" in DAN Isolation and Its Implication for Museum Collections" Museum of Texas Tech University, No. 163, May 1, 1997.

463a. EDTA-Medium, 2010 DSMZ Gmbh.

Tabak et al., "A Revolution in Biomedical Assessment: The Development of Salivary Diagnostics" Journal of Dental Education, Dec. 2001.

Goldenberger et al., "A Simple "Universal" DNA Extraction Procedure Using SDS and Proteinase K Is Compatible with Direct PCR Amplification" PCR Methods and Applications, Received Dec. 12, 1997; accepted Mar. 31, 1995.

Garcia-Closas et al., "Collection of Genomic DNA from Adults in Epidemiological Studies by Buccal Cytobrush and Mouthwash" Cancer Epidemiology, Biomarkers and Prevention, vol. 10, 687-696, Jun. 2001.

Freeman et al., "DNA by Mail: An Inexpensive and Noninvasive Method for Collecting DNA Samples from Widely Dispersed Populations" Behavior Genetics, vol. 27, No. 3 1997.

Johnson et al., "Effectiveness of alcohol-based hand rubs for removal of Clostridium difficile spores from hands", Infect Control Hosp Epidemiol, Jun. 2010.

Rymaszewski et al., "Estimation of cellular DNA content in cell lysates suitable for RNA isolation" Analytical Biochemistry, vol. 188, Issue 1, Jul. 1990, pp. 91-96.

Excerpts from The American Heritage Dictionary, 2000.

(56) References Cited

OTHER PUBLICATIONS

Monahan et al., "Extraction of RNA from Intracellular *Mycobacterium tuberculosis*" Methods in Molecular Medicine, vol. 54: *Mycobacterium tuberculosis* Protocols; 2001.
Maniatis et al., "Isolation of MRNA From Mammalian Cells", 1982.
Kilpatrick et al, "Noncryogenic Preservation of Mammalian Tissues for DNA Extraction: An Assessment of Storage Methods" Biochemical Genetics, vol. 40, Nos. ½, Feb. 2002.
Streckfus et al., "Saliva as a diagnostic fluid" 2002.
Thermo Fisher Scientific, "Top 10 Ways to Improve Your RNA Isolation", Downloaded on or around Nov. 22, 2021.
Piotr Chomczynsk, et al., "Single-Step Method of RNA Isolation by Acid Guanidinium Thiocyanate-Phenol-Chloroform Extraction" Analytical Biochemistry 162, 156-159; 1987.
Feramisco et al., "Co-existence of Vinculin and a Vinculin-like Protein of Higher Molecular Weight in Smooth Muscle" The Journal of Biological Chemistry, vol. 257, No. 18, Issue of Sep. 25, pp. 11024-11031, 1982.
Woldringh et al., "Effects of Treatment with Sodium Dodecyl Sulfate on the Ultrastructure of *Escherichia coli*" Journal of Bacteriology, Sep. 1972.
Rutala et al., "Guideline for Disinfection and Sterilization in Healthcare Facilities, 2008".
Breslow et al., "On the mechanism of action of ribonuclease A: Relevance of enzymatic studies with a p-nitrophenylphosphate ester and a thiophosphate ester" Proc. Natl. Acad. Sci. USA., vol. 93, pp. 10018-10021, Sep. 1996.
Farrell, "RNA Methodologies A Laboratory Guide for Solation and Aracterization Chapters 4 and 5" Copyright Elsevier 2021.
Noll et al., "The Use of Sodium and Lithium Dodecyl Sulfate in Nucleic Acid Isolation" Methods in Enzymology, vol. XII, Nucleic Acids, Part B, 1968.
Zou, "A Practical Approach to Genetic Screening for Influenza Virus Variants", Journal of Clinical Microbiology, vol. 25, No. 10, Oct. 1997, p. 2623-2627.
Ausubel et al., "Analysis of Protein Interactions", Current Protocols in Molecular Biology, Dec. 4, 2003.
Cunningham et al., "Colorectal Cancer Methods and Protocols" Methods in Molecular Medicine, vol. 50; 2001.
Loens et al., "Detection of Mycoplasma pneumoniae in Spiked Clinical Samples by Nucleic Acid Sequence-Based Amplification" Journal of Clinical Microbiology, Apr. 2002, p. 1339-1345.
Spectrum Solutions, "FDA Emergency Use Authorization Granted Utilizing Saliva for COVID-19 Testing Exlcusively Using SDNA-1000Saliva Collection Device from Spectrum" Apr. 13, 2020.
Fisher Catalog 1998-1999.
Brady, Chapter 16 Acid-Base Equilibria in Aqueous Solutions, "General Chemistry Principles and Structure Buffers: the control of pH" 1990.
Chirgwin et al."Isolation of Biologically Active Ribonucleic Acid from Sources Enriched in Ribonuclease", Biochemistry vol. 18, No. 24, 1979.
Maniatis et al., "Molecular Cloning a Laboratory Manual" Cold Spring Harbor Laboratory; 1982.
Ausubel et al.,"Preparation and Analysis of RNA" Current Protocols in Molecular Biology, Dec. 4, 2003.
Promega 1993-1994 Catalog, Revolutions in Science.
Boom et al., "Rapid and Simple Method for Purification of Nucleic Acids", Journal of Clinical Microbiology, Apr. 1990.
Shahbazi et al., "Screening of SDS-degrading bacteria from car wash wastewater and study of the alkylsulfatase enzyme activity", Iranian Journal of Microbiology, vol. 5 No. 2, Jun. 2013, pp. 153-158.
Yuan et al., "Statistical Analysis of Real-Time PCR Data " BMC Bioinformatics, Feb. 22, 2006.
Spectrum Solutions, "Technically Superior Whole Saliva Collection Devices, accessed on Nov. 20, 2020".
Sela et al., "The Correlation of Ribonuclease Activity with Specific Aspects of Tertiary Structure" Biochimica et Biophysica Acta, vol. 26, 1957.
Cox et al., "The Use of Guanidinium Chloride in the Isolation of Nucleic Acids" Methods in Enzymology, vol. XII, Nucleic Acids, Part B, 1968.
International Preliminary Reporton Patentability received for PCT Patent Application No. PCT/US2019/062484, dated Jun. 3, 2021, 8 pages.
European Search Report received for EP Patent Application No. 19887385.3, dated Aug. 8, 2022, 10 pages.
International Preliminary Report on Patentability received for PCT Patent Application No. PCT/US2020/038858, dated Dec. 30, 2021, 9 pages.
Jennings et al., Petition for Inter Partes Review of Patent No. 11,002,646, Jul. 29, 2022.

* cited by examiner

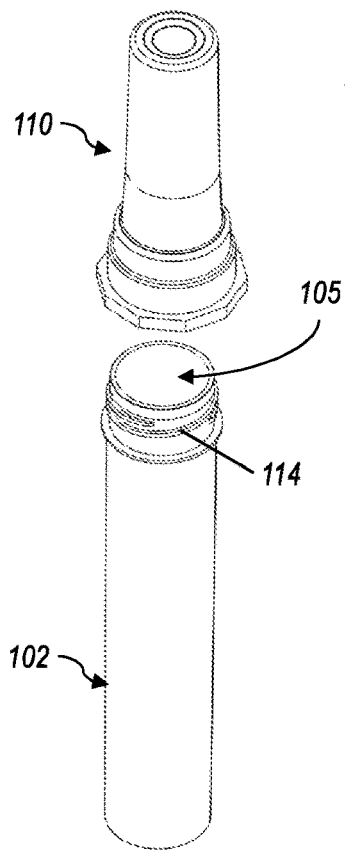
FIG. 1A
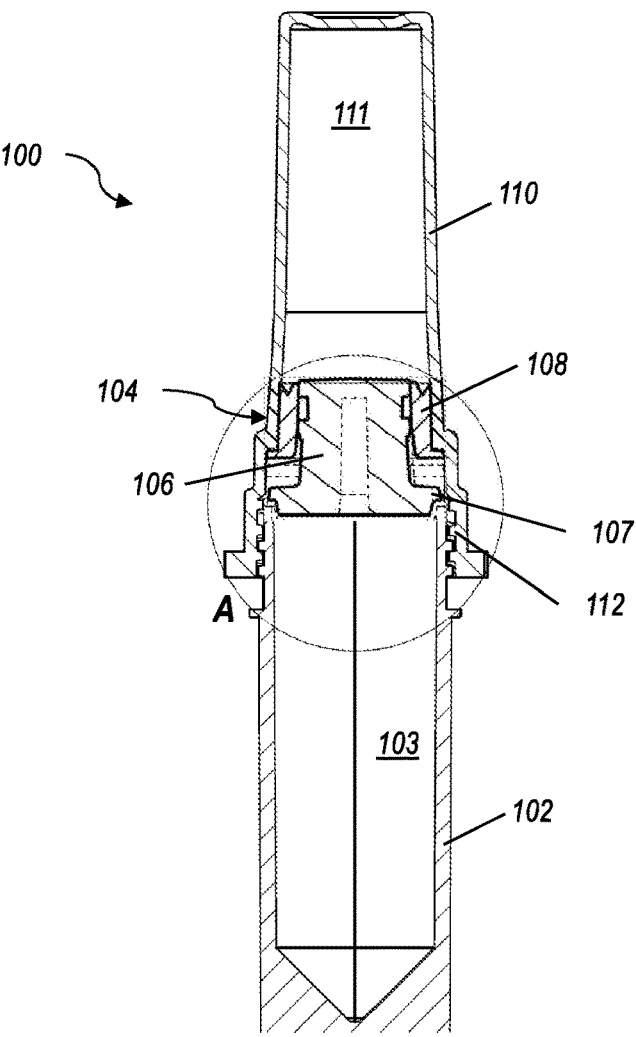
FIG. 1B
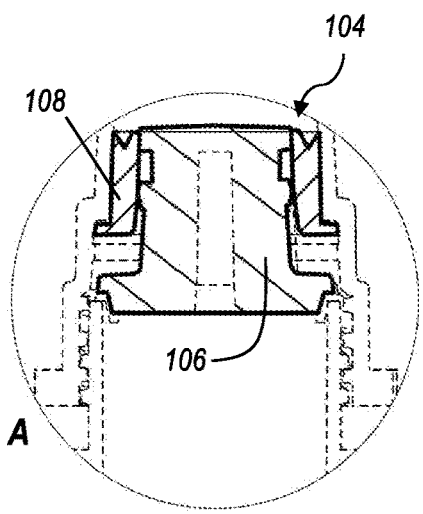
FIG. 2A
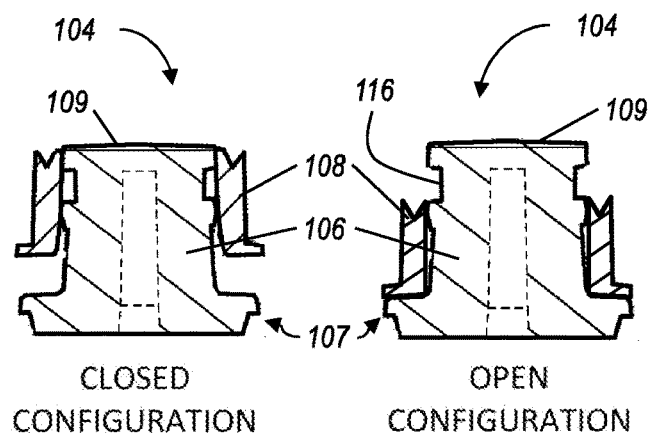
CLOSED CONFIGURATION
FIG. 2B
OPEN CONFIGURATION
FIG. 2C

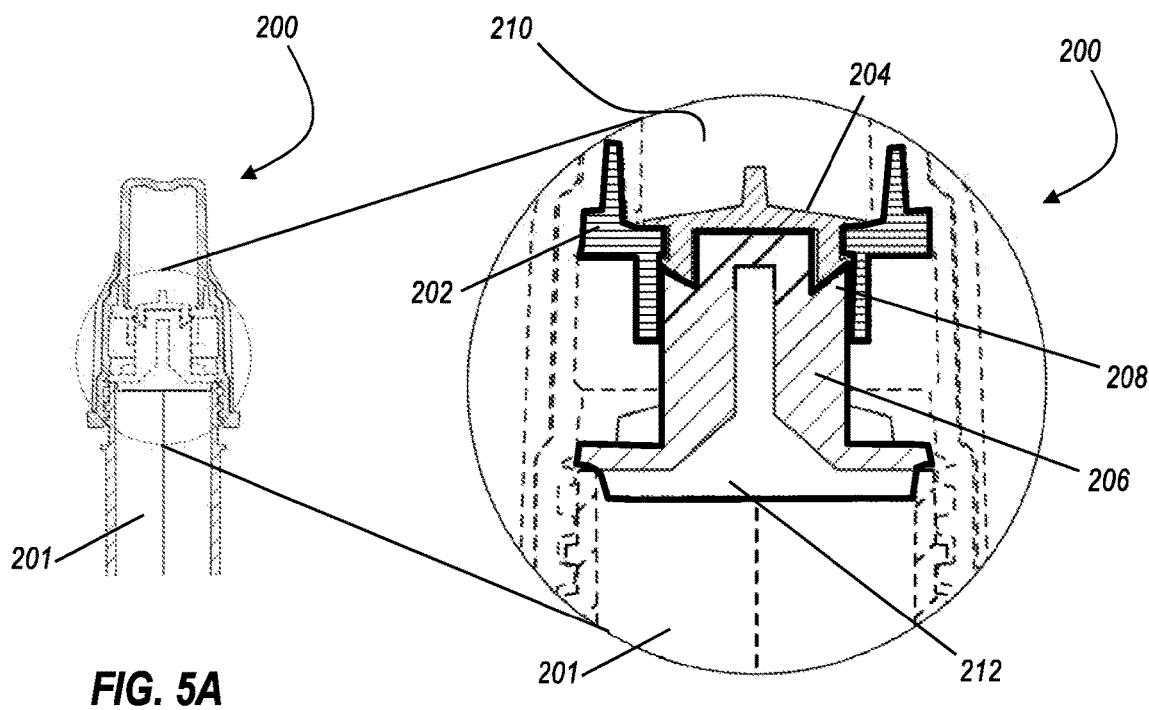
FIG. 5A
FIG. 5B
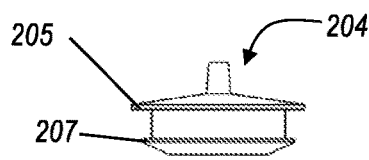
FIG. 6
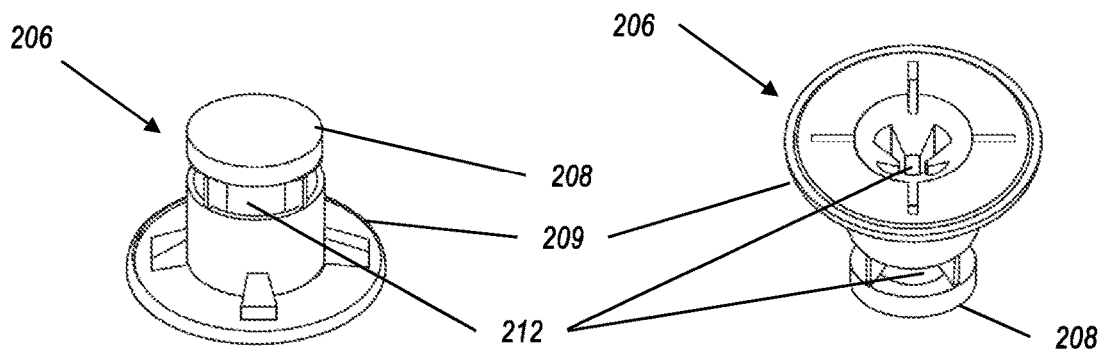
FIG. 7A  FIG. 7B

METHOD OF COLLECTING AND PRESERVING A BIOLOGICAL SAMPLE

CROSS-REFERENCE TO RELATED APPLICATION

This application is a division of U.S. patent application Ser. No. 17/093,815, filed Nov. 10, 2020, which is a continuation of U.S. patent application Ser. No. 16/906,830, filed Jun. 19, 2020, which claims the benefit of U.S. Provisional Application No. 62/864,500, filed Jun. 20, 2019, which are incorporated by reference in their entirety.

BACKGROUND

Technical Field

This disclosure generally relates to vials and vessels for collecting and storing biological samples. More specifically, the present disclosure relates to systems and kits for the collection and preservation of biological samples for future testing in a laboratory or other biological sample analysis facility.

Background and Relevant Art

Field collection of biological samples can provide scientists, physicians, geneticist, epidemiologists, or similar personnel with invaluable information. For example, access to a fresh sample of a patient's blood, purulent discharge, or sputum can help a physician or epidemiologist to isolate or identify a causative agent of infection. Similarly, a saliva sample can permit a scientist or geneticist access to the requisite nucleic acid for genetic sequencing, phylotyping, or other genetic-based studies. In the foregoing examples, in addition to many other situations, it is desirable to work with a fresh biological sample to ensure procurement of accurate results. However, isolation of the probative composition (e.g., nucleic acid, proteins, chemicals, etc.) often requires use of specialized equipment and often benefits from controlled laboratory conditions.

It can be inconvenient and sometimes improbable to require patients/individuals to travel to a biological sample collection center having the appropriate equipment and desirable controlled environment for sample preparation. Similarly, it may be difficult for personnel to directly access the patient/individual, particularly if the sample size is large and/or geographically diverse (e.g., as can be found in large genetic studies of thousands of individuals across an entire country, ethnic population, or geographic region). Further complicating this issue, it is often beneficial to immediately process any procured biological sample, and field personnel may be limited by lack of access to appropriate specialized equipment or to a controlled environment for high-fidelity sample processing.

Some biological sample collection devices and kits have addressed some of the foregoing issues. For example, some commercial kits provide a user with a vial for receiving a biological sample and a preservation reagent that can be added to the collected biological sample, acting to preserve elements within the biological sample (to a certain extent and for a period of time). However, implementations of self-collection systems often rely on inexperienced or untrained individuals to deposit the biological sample into the receiving vessel. This presents a number of problems, including, for example, technical training and precise measurements often required to properly preserve the biological sample for later processing. In the absence of such, it is important to provide a biological sample collection system that can be easily implemented by a novice user and which can preserve the received biological sample for later processing.

Accordingly, there are a number of disadvantages with biological sample collection and preservations systems that can be addressed.

BRIEF SUMMARY

Implementations of the present disclosure solve one or more of the foregoing or other problems in the art with kits, apparatuses, and methods for collecting and preserving a biological sample. In particular, one or more implementations can include a biological sample collection system—or a kit including the same—for collecting and preserving a biological sample.

In some embodiments, a biological sample collection system can include a sample collection vessel having an opening for receiving a biological sample, a selectively movable valve comprising a core and a collar disposed about the core that is configured to at least partially associate with the opening of the sample collection vessel, and a sealing cap configured to associate with the selectively movable valve and with the sample collection vessel. The sealing cap can include a reagent chamber for storing a measure of sample preservation reagent. Associating the sealing cap with the sample collection vessel causes a physical rearrangement of the core relative to the collar such that a fluid vent associated with the core is moved into fluid communication with the reagent chamber, thereby permitting sample preservation reagent to pass from the regent chamber to the sample collection vessel.

In other embodiments, a biological sample collection system can include a sample collection vessel having an opening for receiving a biological sample and a plug assembly. The plug assembly can include a post having a fluid vent that is configured to at least partially associate with the opening of the sample collection vessel and a plug associated with the post that obscures the fluid vent in a closed configuration of the plug assembly. The biological sample collection system can additionally include a sealing cap configured to associate with the plug assembly and with the sample collection vessel. The sealing cap can include a reagent chamber for storing a measure of sample preservation reagent. Associating the sealing cap with the sample collection vessel can cause a physical rearrangement of the plug assembly such that the plug is removed from association with the post, thereby permitting sample preservation reagent to pass from the regent chamber to the sample collection vessel.

The present disclosure also includes methods for collecting and preserving a biological sample. An exemplary method includes receiving a biological sample at a disclosed sample collection system and associating a sealing cap with the sample collection vessel, for example, to cause a selectively movable valve associated with the sealing cap to open and thereby release sample preservation reagent held within the sealing cap into the sample collection chamber or to cause the plug of a plug assembly to dislodge, thereby releasing reagent held within the sealing cap into the sample collection chamber.

Accordingly, systems, methods, and kits for collecting a biological sample are disclosed herein. This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 1A illustrates a perspective view of an unassembled three-dimensional model of an exemplary sample collection system with the depicted sealing cap unsecured from the sample collection vessel in accordance with one or more embodiments of the present disclosure.

FIG. 1B illustrates a cross-sectional view of an assembled three-dimensional model of the sample collection system of FIG. 1A with the depicted sealing cap secured to a sample collection vessel and the associated valve in a closed configuration in accordance with one or more embodiments of the present disclosure.

FIG. 2A illustrates a cross-sectional view of the selectively movable valve of FIG. 1B depicted in a closed configuration in accordance with one or more embodiments of the present disclosure.

FIG. 2B illustrates a cross-sectional view of the selectively movable valve of FIGS. 1B and 2A isolated away from other components of the sample collection system and depicted in a closed configuration in accordance with one or more embodiments of the present disclosure.

FIG. 2C illustrates a cross-sectional view of the selectively movable valve of FIGS. 1B and 2A isolated away from other components of the sample collection system and depicted in an open configuration in accordance with one or more embodiments of the present disclosure.

FIG. 5A illustrates a cross-sectional view of an assembled three-dimensional model of another sample collection system with the depicted sealing cap secured to a sample collection vessel and the associated plug assembly in a closed configuration.

FIG. 5B is a zoomed view of a portion of the plug assembly and sealing cap as shown in FIG. 5A.

FIG. 6 illustrates a three-dimensional rendering of an exemplary plug.

FIGS. 7A and 7B illustrate perspective views of an exemplary post of a plug assembly.

DETAILED DESCRIPTION

Figures 3A, 3B:
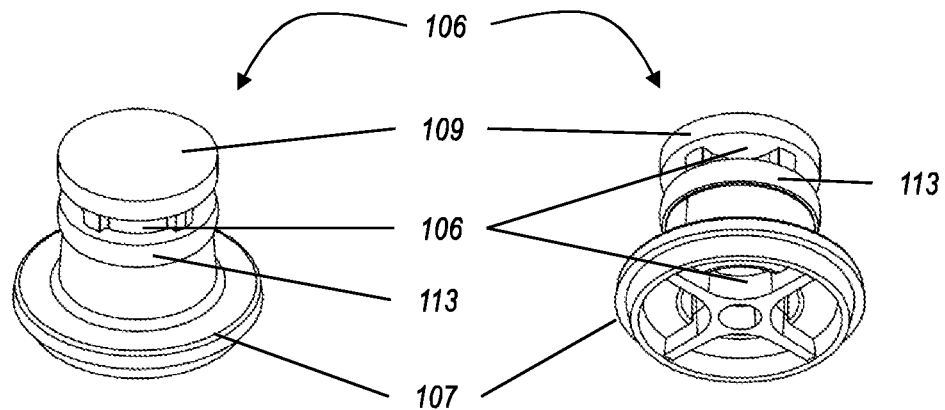
FIGS. 3A and 3B illustrate perspective views of a core component of a selectively movable valve in accordance with one or more embodiments of the present disclosure.
Figures 4A, 4B:
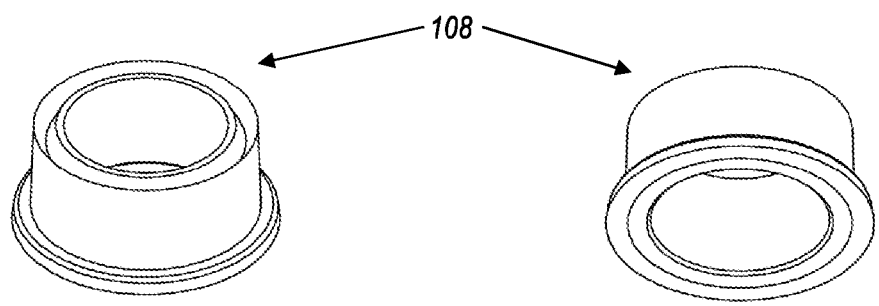
FIGS. 4A and 4B illustrate perspective views of a collar component of a selectively movable valve in accordance with one or more embodiments of the present disclosure.

Embodiments of the present disclosure address one or more problems in the art of systems, kits, and/or methods for collecting and preserving a biological sample. A biological sample can be collected and its contents evaluated for various reasons, including, for example, identifying or characterizing a causative agent of disease (e.g., for treatment of the affected individual, for epidemiological reasons, etc.) or for genetic analysis of a subject's nucleic acid (e.g., genetic phylotyping, gene expression studies, genome sequencing, etc.). In most instances, including within the foregoing examples, it is desirous that the fidelity of the biological sample be maintained so that it retains its probative value. However, collecting and preparing biological samples for analysis has traditionally been a complex endeavor for the skilled technician or specialized professional. This is problematic for obvious reasons, including the time and cost associated with individually collecting and transporting biological samples, particularly when the subjects reside in disparate rural locations and require service from personnel with the proper skill set to properly collect and preserve the biological sample.

Embodiments of the present disclosure provide sample collection and preservation systems and kits, and methods for using the same, which address one or more of the foregoing problems. For example, utilizing systems, kits, and methods for collecting and preserving biological samples, as disclosed herein, removes the need of specialized personnel when collecting and initially preserving a biological sample. Furthermore, the disclosed embodiments simplify sample collection and preservation, which decreases the likelihood that even an unskilled user will err when collecting and preserving a biological sample.

As an illustrative example of the foregoing, biological sample collection kits disclosed herein include at least a two-piece sample collection and preservation system. A first portion includes a sample collection vessel or vessel, which can be detachably associated with a funnel. When used, the funnel acts to guide the receipt of a biological sample from a user into the sample collection chamber of the collection vessel or vessel. The funnel can also make it easier for a user to engage the collection vessel and deposit a biological sample into the sample collection chamber. After depositing the requisite amount of biological sample (which may be indicated by a mark on the sample collection vessel), a user can remove the funnel (if used) and associate the second portion of the two-piece sample preservation system—e.g., a sealing cap associated with a selectively movable valve or plug assembly—with the collection vessel. The reagent chamber of the sealing cap is pre-filled with a predetermined amount of sample preservation reagent, and as the sealing cap is drawn down to seal the received biological sample within the sample collection chamber of the collection vessel, the selectively movable valve or plug assembly enters an open configuration and the preservation reagent is released from the reagent chamber, through fluid vents in the valve core or plug assembly post, and into the sample collection chamber where it mixes with and preserves the received biological sample.

As described in more detail below, the selectively movable valves and valve assemblies can independently be opened (depending on the embodiment incorporating the same) to release reagents from the reagent chamber into the sample collection chamber.

With respect to embodiments having a selectively movable valve, the collar of the selectively movable valve is mechanically interlocked (e.g., via a friction fit) with the sealing cap such that the collar moves in unison with the sealing cap. The collar can be annular and surround the valve core forming a fluid tight connection therebetween. A flange associated with the core is sized and shaped to fit over the opening of the sample collection vessel (or structure associated therewith), preventing its ingress into the sample collection chamber. Upon association of the sealing cap with the sample collection vessel, the core flange abuts the opening of the sample collection chamber. As the sealing cap is further secured to the sample collection vessel (e.g., by threaded engagement), the collar moves in conjunction with the sealing cap, and the core remains stationary in relation to the sample collection vessel. In this way, the core moves (e.g., translates longitudinally) relative to the collar and sealing cap, causing the selectively movable valve to open (e.g., by undergoing a physical rearrangement). The independent movement of core relative to the sealing cap can be enabled by, for example, the force (e.g., frictional force or force required to overcome a mechanical interlock) between the core and the collar (which forms a fluid tight connection) being less than the force between the attachment mechanisms of the sealing cap and sample collection device. When moved to an open configuration, the previously obstructed fluid vents provided by the core are at least partially unobstructed, thereby creating a conduit for communicating the sample preservation solution from the reagent chamber of the sealing cap into to the sample collection chamber.

It should be appreciated that in some embodiments, opening of the selectively movable valve is reversible. That is, the selectively movable valve can be moved from an open configuration to a closed configuration. For example, embodiments of the disclosed apparatus can be configured so that the core can be manually repositioned within the collar (e.g., by applying a longitudinal force against the head member of the core and toward the collar), thereby returning the selectively movable valve to the closed configuration.

With respect to embodiments having a plug assembly, a collar of the plug assembly is mechanically interlocked (e.g., via a friction fit) with the sealing cap such that the collar moves in unison with the sealing cap. The collar can be annular and surround the post of the plug assembly and may form a fluid tight connection therebetween. Additionally, or alternatively, a plug can be positioned within the aperture formed by the collar, forming a fluid tight connection therebetween. The plug can have a head sized and shaped to overlay a portion of the top surface of the collar (forming a fluid tight connection therebetween) and/or can have a plug body sized and shaped to fit within the aperture formed by the collar such that a fluid tight connection is formed between the plug body and a sidewall of the collar (e.g., a sidewall defining the aperture). A flange associated with the post is sized and shaped to fit over the opening of the sample collection vessel (or structure associated therewith), preventing its ingress into the sample collection chamber. Upon association of the sealing cap with the sample collection vessel, the post flange abuts the opening of the sample collection chamber. As the sealing cap is further secured to the sample collection vessel (e.g., by threaded engagement), the collar moves in conjunction with the sealing cap, and the post remains stationary. In this way, the post moves (e.g., translates longitudinally) relative to the collar and sealing cap, causing the post to abut against and apply pressure to the plug, eventually causing the plug to dislodge from the collar and enter into the reagent chamber. The independent movement of post relative to the sealing cap can be enabled by, for example, the force (e.g., frictional force or force required to overcome a mechanical interlock) between the post and the collar and/or plug (which forms a fluid tight connection) being less than the force between the attachment mechanisms of the sealing cap and sample collection device. When moved to an open configuration, the previously obstructed fluid vent formed by the post is at least partially unobstructed, thereby creating a conduit for communicating the sample preservation solution from the reagent chamber of the sealing cap into to the sample collection chamber.

As can be appreciated from the foregoing, in addition to alternative and/or additional embodiments provided herein, the systems, kits, and methods of the present disclosure can be used by skilled or unskilled individuals with reduced likelihood of error associated with collecting and at least initially preserving a biological sample. Accordingly, implementations of the present disclosure can reduce the cost associated with procuring biological samples for diagnostic, scientific, or other purposes and can increase the geographic reach of potential sample collection areas without the need of establishing the necessary infrastructure (e.g., controlled environments conducive to sample collection and preservation, skilled personnel to physically collect, transport, and/or preserve the biological samples, etc.).

As used herein, the term "biological sample" can include any cell, tissue, or secretory fluid (whether host or pathogen related) that can be used for diagnostic, prognostic, genetic, or other scientific analysis. This can include, for example, a human cell sample such as skin. It can also include a non-human cell sample that includes any of a bacterium, virus, protozoa, fungus, parasite, and/or other prokaryotic or eukaryotic symbiont, pathogen, or environmental organism. The term "biological sample" is also understood to include fluid samples such as blood, urine, saliva, and cerebrospinal fluid and extends to other biological samples including, for example, mucus from the nasopharyngeal region and the lower respiratory tract (i.e., sputum).

As used herein, the "probative component" of the biological sample refers generally to any protein, nucleic acid, surface moiety, or other compound that can be isolated from the biological sample. Preferably, the probative component is or includes nucleic acid, more preferably DNA. In a preferred embodiment, the biological sample is or includes saliva, which presumptively contains a preferable probative component in the form of the user's genetic material (e.g., DNA and RNA).

Sample Collection Systems and Kits Having a Selectively Movable Valve

In one embodiment, a biological sample is collected, preserved, and stored in a collection vessel as part of a multi-piece sample collection system or kit. An example of a sample collection device similar to the embodiment illustrated in FIGS. 1-4 is set forth in U.S. Design application No. 29/698,615, filed Jul. 18, 2019, which is incorporated by reference. An example of a sample collection device similar to the embodiment illustrated in FIGS. 5-7 is set forth in U.S. Design application No. 29/698,614, filed Jul. 18, 2019, which is incorporated by reference.

As shown in FIG. 1A, a first piece of the system 100 or kit can include a sample collection vessel 102, a second piece includes a sample collection funnel (not shown), which may be packaged separately from or removably connected to the collection vessel, and a third piece includes a sealing cap 110 having a reagent chamber disposed within or integrated with the sealing cap selectively and a selectively movable valve comprised of a core and a collar. The sealing cap 110 is configured to associate with the sample collection vessel 102, to dispense sample preservation reagents into the sample collection vessel 102 through the selectively movable valve, and to seal the contents of the sample collection chamber therein.

For example, FIG. 1B illustrates a cross-sectional view of an assembled three-dimensional model of the sample collection system 100 of FIG. 1A. The system 100 includes a sample collection vessel 102 and optionally, a funnel (not shown), which can be associated with a top portion or opening 105 of the sample collection vessel 102 and thereby allow fluid communication with the sample collection chamber 103 of the sample collection vessel 102. The biological sample collection system 100 can also include a selectively movable valve 104 comprised of a core 106 and a collar 108 associated with the sealing cap 110 that has a reagent chamber 111 disposed within or integrated with the sealing cap 110. The sealing cap 110—together with the selectively movable valve 104—can be sized and shaped to associate with a top portion of the collection vessel 102 such that the cap 110 fits over and seals an opening 105 of the sample collection chamber 103 and at least a portion of the valve 104 (e.g., a flange 107 of the core 106) extends over the opening 105 of the sample collection chamber 103.

In some embodiments, the reagent within the reagent chamber 111 includes a preservation or buffering solution that protects the integrity of the probative component of the biological sample prior to purification or testing. Examples of preservation reagents that can be used in conjunction with the sample collection systems described herein are disclosed in U.S. Pat. No. 10,174,362, US Pat. Pub. No. 2019/0062806, and WO 2020/102570, which are incorporated by reference. Preservation reagents are typically chemical solutions and may contain one or more salts (e.g., NaCl, KCl, $Na_2HPO_4$, $KH_2PO_4$, or similar, and which may, in some implementations, be combined as a phosphate buffered saline solution, as known in the art), lysing agents (e.g., detergents such as Triton X-100 or similar), chelating agents (e.g., ethylenediaminetetraacetic acid (EDTA), ethylene glycol-bis(β-aminoethyl ether)-N,N,N',N'-tetraacetic acid (EGTA), or similar), distilled water, or other reagents known in the art.

In one or more embodiments, the reagent or buffering solution stabilizes at least one probative component within the sample (e.g., nucleic acids, such as DNA and RNA, protein, etc., and combinations thereof) during transfer, transportation, and/or storage at a laboratory, clinic, or other destination. After the preservation solution is added, the sample can be stored at or below room temperature for weeks or months without significant loss of the probative component. That is, the sample can still be utilized for diagnostic, genetic, epidemiologic, or other purposes for which it was collected after storage for weeks or months in the preservation solution.

With continued reference to FIG. 1, the sealing cap 110 and a saliva funnel (not shown) can each independently attach to the sample collection vessel 102 using a connection mechanism. The connection mechanism can include, for example, threads, snap or press fit connections, tongue and groove members, bayonet connection, or other interlocking or mechanically coupling mechanisms. For example, a funnel can be first attached to the sample collection vessel 102 via complementary connection mechanisms (e.g., complementary threads; not shown). After facilitating receipt of a biological sample from a user, the funnel can be removed by reversing the complementary connection mechanism (e.g., unscrewing the funnel; not shown), and a sealing cap 110 can be secured to the collection vessel 102 using a same or similar complementary connection mechanism. For example, as shown in FIGS. 1A and 1B, the sealing cap 110 can include connection members 112 (e.g., threads) located on an inner circumferential wall of the sealing cap 110 that are complementary to and work in conjunction with the connection members 114 (e.g., complementary threads) disposed on an exterior surface of the sample collection vessel 102.

In some embodiments, the connection mechanism between the funnel and collection vessel is different than the connection mechanism between the solution cap and the collection vessel. For example, the funnel may be press fit or snap fit onto the collection vessel, whereas the solution cap is rotationally secured through engagement of complementary threads located on an exterior portion of the collection vessel and an interior portion of the solution cap or vice versa. Regardless of the attachment mechanism used, a sample preservation fluid can be introduced into the sample collection chamber 103 and mixed with the deposited biological sample as a result of the sealing cap 110 being attached to the sample collection vessel 102. As provided earlier, this can be due to the selectively movable valve 104 opening and allowing reagent to be released through fluid vent 116 defined by the open valve 104 and into the sample collection chamber 103.

The sealing cap 110 is configured to receive a measure of reagents into the reagent chamber 111, and as shown by the cross-sectional views of the assembled sample collection system 100 in FIG. 1B, a selectively movable valve 104 is associated with the sealing cap 110. The collar 108 can be snap-fittingly received into the sealing cap 110, creating a fluid tight connection therebetween. As illustrated, the collar 108 includes a retaining ring or flange that engages the sealing cap 110 to stabilize the collar 108.

As further illustrated by FIGS. 2A-2C, the core 106 defines a fluid vent 116, and when the valve 104 is in a closed configuration (as shown in FIGS. 2A and 2B), any reagent disposed within the reagent chamber 111 is retained and sealed within the reagent chamber 111. The valve 104 is shown in FIGS. 1B, 2A, and 2B as being aligned in a closed configuration. However, as shown in FIG. 2C, the selectively movable valve 104 can be arranged in an open configuration. When associated with the sealing cap 110 in an open configuration, reagent may be transferred from the reagent chamber 111 to the sample collection chamber 103 through the vent(s) 116.

That is, the fluid vent(s) 116 can be obstructed by the collar 108 of the selectively movable valve 104 when the valve 104 is in a closed configuration, as illustrated in FIGS. 2A and 2B. In this state, the interaction between the interior sidewall of the collar 108 and the head member 109 of the core 106 creates a fluid tight connection—at least at and/or around the fluid vent 116. The fluid tight connection between the collar 108 and the core 106 prevents the premature or unintentional expulsion of reagent from the reagent chamber 111.

It should be appreciated that in some embodiments, the fluid vent(s) and/or structure of the core can beneficially act as an agitator of fluids entering and/or traversing between the sample collection chamber and the sealing cap.

As the complementary threads 114, 112 between the sealing cap 110 and the sample collection vessel 102 are inter-engaged and the sealing cap 110 is advanced towards the sample collection vessel 102, the proximal flange 107 of the core 106 engages the upper lip of the sample collection tube defining the opening 105 thereof. As the sealing cap 110 is further secured to and moved toward the sample collection vessel 102 (e.g., by threaded engagement), the collar 108 moves in conjunction with the sealing cap 110, and the core 106 remains stationary relative to the sample collection vessel 102. In this way, the collar 108 is displaced longitudinally relative to the core 106, causing the selectively movable valve assembly 104 to enter an open configuration (e.g., by undergoing a physical rearrangement as shown in FIG. 2C). When moved to the open configuration, the previously obstructed fluid channels or vents 116 formed within the core 106 allow fluid communication between the reagent chamber 111 and the sample collection chamber 103.

The fluid channels/vents 116 formed within the core 106, and the various other components of the core 106 discussed above are illustrated in the perspective views of an exemplary core 106 in FIGS. 3A and 3B. Similarly, the collar 108 of FIGS. 1 and 2 is illustrated in multiple perspective views comprising FIGS. 4A and 4B.

As the core 106 transitions from the closed configuration to the open configuration, an annular retention element 113 disposed on the body of the core 106 forms a fluid tight seal with the inner sidewall of the collar 108. Upon fully entering the open configuration, the annular retention element 113 is flush with the top surface of the collar 108 and maintains a fluid-tight connection therebetween. Accordingly, there is no pooling of sample preservation reagent (from the fluid chamber) between the interior sidewall of the collar 108 and the exterior sidewall of the core 106. Instead, the sample preservation reagent is directed from the reagent chamber 111, through the fluid vents 116 formed within the core 106, and into the sample collection chamber 103 it mixes with and preserves the received biological sample. In this way, the valve assembly 104 can move from a closed configuration to an open configuration when the sealing cap 110 is sealed onto the sample collection vessel 102.

In some embodiments, the resistive force derived from the engagement of the collar 108 with the chamber sidewall is the result of an interference fit formed between the collar 108 and the chamber sidewall. The interference fit can, in some embodiments, be a fluid-tight fit.

In some embodiments, the rotational distance required to open the selectively movable valve 104 is proportional to the distance required to at least partially unobstruct the fluid vent 116. This distance may be the same or less than the distance traversed by the sealing cap 110 from initial engagement of the connection members 114, 112 to a sealed position of the cap 110 and vessel 102. However, it should be appreciated that although a plurality of fluid vents 116 are illustrated in the Figures, in some embodiments there can be fewer (e.g., a single fluid channel/vent or more than four fluid channels/vents).

Sample Collection Systems and Kits Having a Plug Assembly

Referring now to FIGS. 5-7, some sample collection systems can include a plug assembly. As shown, the hollow collar 202 of the plug assembly is mechanically interlocked (e.g., via a friction fit) with the sealing cap 210 such that the hollow collar 202 moves in unison with the sealing cap 210 toward the sample collection vessel 201 when the sealing cap 210 is used to seal the sample collection vessel 201. As shown in FIGS. 5A, 5B, and 6, the plug 204 includes a cylindrical body and two flanges. An upper flange 205 is sized and shaped to span the aperture formed by the hollow collar 202 and can, as shown, extend beyond the diameter of the collar's aperture such that a bottom surface of the upper flange 205 can form a fluid tight seal with the upper surface of the hollow collar 202. A lower flange 207 of the plug 204 extends radially from the cylindrical body and is sized and shaped to engage the sidewall of the hollow collar 202 defining the aperture.

The post 206 defines a plurality of fluid vents 212 that pass uninterrupted through the body of the post 206. A cylindrical upper portion of the post is sized and shaped to fit within the aperture defined by the hollow collar 202. A leading edge 208 of the upper portion of the post 206 is configured to associate with a bottom surface (e.g., the lower flange 207) of the plug 204. In the embodiment shown in FIGS. 5A and 5B, the leading edge 208 of the upper portion includes a crown that engages an indent formed within the bottom portion of the plug 204. In some embodiments, the outer rim of the crown is sized and shaped to engage the lower flange 207 of the plug 204. The post 206 additionally includes a base portion or flange 209 that is sized and shaped to engage the opening of the sample collection vessel (or structure associated therewith).

When provided to a user for collecting a biological sample (typically saliva), the plug-disc device (e.g., device 200) is included in two parts: (1) the sample collection vessel 201 and (2) the sealing cap 210, which includes the seal assembly (in a sealed configuration) forming a fluid-tight seal over the reagent chamber where it retains pre-loaded sample preservation solution. The user can deposit the biological sample within the sample collection tube, and following use, the sealing cap is associated with the sample collection tube to seal the received biological sample.

Upon association of the sealing cap 210 with the sample collection vessel 201, the base portion or flange 209 of the post 206 engages the upper lip of the sample collection vessel defining the opening thereof. As the sealing cap 210 is further secured to and moved toward the sample collection vessel 201 (e.g., by threaded engagement), the hollow collar 202 moves in conjunction with the sealing cap 210, and the post 206 remains stationary relative to the sample collection vessel 201. In this way, the hollow collar 202 is displaced longitudinally with respect to the post 206, and this causes the leading edge 208 (e.g., crown portion) of the post 206 to press against the bottom side (e.g., lower flange 207) of the plug 204. At some point, the rotational force of tightening the sealing cap 210 is translated into a force sufficient to cause the plug 204 to disengage from the hollow collar 202. At first, the upper flange 205 is translated away from the hollow collar 202, thereby breaking the fluid-tight seal formed therebetween, while the second, lower flange 207 remains in contact with the sidewall of the hollow collar 202. Eventually, however, the post 206 presses—and moves—the plug 204 such that the lower flange 207 becomes disengaged from the sidewall, causing the plug 204 to be ejected into the reagent chamber of the sealing cap 210.

Once the plug 204 is disengaged from the hollow collar 202, the upper end of the post 206 is brought into fluid communication with the reagent chamber—essentially converting the seal assembly to an unsealed configuration. In this unsealed configuration, the fluid vents 212 are unobstructed and act as channels for transporting the sample preservation solution from the reagent chamber to the sample collection vessel 201. The body of the post 206 forms a fluid tight seal with the inner sidewall of the hollow collar 202, forcing egress of sample preservation solution through the fluid vents/channels 212. Accordingly, there is no pooling of sample preservation reagent (from the reagent chamber) between the interior sidewall of the hollow collar 202 and the exterior sidewall of the post 206. Instead, the sample preservation reagent is directed from the reagent chamber, through the fluid vents 212 formed within the post 206, and into the sample collection vessel 201 where it mixes with and preserves the received biological sample. In this way, the seal assembly can move from a sealed configuration to an unsealed configuration when the sealing cap 210 is sealed onto the sample collection vessel 201.

In some embodiments, the seal assembly can be reversibly sealed and unsealed. That is, the plug 204 from the seal assembly can be serially added and removed from the opening of the hollow collar 202 to iterate from the sealed configuration to the unsealed configuration. For example, associating the sealing cap 210 with the sample collection vessel 201 can cause the plug 204 to disengage, thereby causing the seal assembly to transition from the sealed configuration to the unsealed configuration. In the unsealed configuration, the post 206 can be retracted and the plug 204 again placed within the hollow collar 202 to transition the seal assembly from the unsealed configuration to the sealed configuration.

Unless defined otherwise, all technical and scientific terms used herein have the same meaning as commonly understood by one of ordinary skill in the art to which the present disclosure pertains.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims.

All changes which come within the meaning and range of equivalency of the claims are to be embraced within their scope.

What is claimed is:

1. A method of collecting and preserving a biological sample, the method comprising:
   providing a sample collection vessel that includes a top portion, an upper lip defining an opening at the top portion, and a sample collection chamber adapted to receive and store a biological sample;
   providing a sealing cap that includes a reagent chamber, a valve assembly, and a sample preservation reagent in the reagent chamber,
      the sealing cap being configured to be associated with the sample collection vessel and fit over and seal the opening at the top portion of the sample collection vessel to thereby seal the contents of the sample collection chamber therein,
      the reagent chamber being disposed within the sealing cap, the reagent chamber storing the sample preservation reagent therein, and
      the valve assembly being disposed within the sealing cap, the valve assembly being configured to retain the sample preservation reagent within the reagent chamber in the sealing cap when the valve assembly is in a closed configuration when the cap is not associated with the sample collection vessel, and the valve assembly being configured to release the sample preservation reagent from the reagent chamber into the sample collection chamber when the sealing cap is associated with the sample collection vessel to put the valve assembly in an open configuration,
      the valve assembly including a core, a plurality of fluid vents, and a collar,
         the core having a first end adjacent to the reagent chamber, a second end opposite the first end configured to associate with the opening at the top portion of the sample collection vessel, a head member at the first end, and a flange at the second end configured to associate with the upper lip of the sample collection vessel,
         the plurality of fluid vents extending through the core in fluid communication with entrance apertures through a side of the head member of the core and exit apertures through the second end of the core, and
         the collar being disposed about the core, the collar forming a fluid-tight seal with the head member of the core and obstructing the entrance apertures to retain the sample preservation reagent within the reagent chamber when the valve assembly is in the closed configuration;
   placing the biological sample through the opening of the sample collection vessel and into the sample collection chamber; and
   associating the sealing cap with the sample collection vessel so that the sealing cap fits over and seals the opening at the top portion of the sample collection vessel to seal the contents of the sample collection chamber,
   wherein associating the sealing cap with the sample collection vessel and moving the sealing cap toward the sample collection chamber causes the flange of the core to associate with the upper lip of the sample collection vessel and prevents further movement of the core toward the sample collection chamber, whereupon further movement of the sealing cap toward the sample collection chamber causes translational movement of the collar along a longitudinal axis relative to the head member of the core to put the valve assembly in the open configuration in which the entrance apertures are at least partially unobstructed by the collar such that the sample preservation reagent is permitted to pass from the reagent chamber, through the entrance apertures and fluid vents, out the exit apertures, and into the sample collection chamber to mix with and preserve the biological sample, and wherein associating the sealing cap with the sample collection vessel causes a physical rearrangement of the core relative to the collar to put the valve assembly in the open configuration in which the one or more fluid vents are at least partially unobstructed and moved into fluid communication with the reagent chamber.

2. The method of claim 1, wherein the physical rearrangement includes translational movement of the core along a longitudinal axis relative to the sealing cap and in a direction opposite the direction of the sealing cap.

3. The method of claim 1, wherein the core and the collar of the valve assembly are configured so that when the sealing cap is associated with the top portion of the sample collection vessel a flange of the core engages the top portion of the sample collection vessel to prevent the core from traversing the opening at the top portion of the sample collection vessel as the sealing cap is moved longitudinally toward the sample collection vessel.

4. The method of claim 1, wherein the core comprises a head member configured to form a fluid-tight seal with the collar when the valve assembly is in the closed configuration, and wherein one or more of the collar or the head member comprises an annular retention element configured to maintain a fluid-tight seal between the collar and the head member when the valve assembly is in the closed configuration.

5. The method of claim 1, wherein the plurality of fluid vents are disposed radially about the core with each comprising an entrance aperture through a side of the core and an exit aperture through a distal end of the core.

6. The method of claim 5, wherein the fluid vents span an interior portion of the core and are uninterrupted between the entrance aperture and the exit aperture of each fluid vent.

7. A method of collecting and preserving a biological sample, the method comprising:
providing a sample collection vessel that includes a top portion, an upper lip defining an opening at the top portion, and a sample collection chamber adapted to receive and store a biological sample;
providing a sealing cap that includes a reagent chamber, a valve assembly, and a sample preservation reagent in the reagent chamber,
the sealing cap being configured to be associated with the sample collection vessel and fit over and seal the opening at the top portion of the sample collection vessel to thereby seal the contents of the sample collection chamber therein,
the reagent chamber being disposed within the sealing cap, the reagent chamber storing the sample preservation reagent therein, and
the valve assembly being disposed within the sealing cap, the valve assembly being configured to retain the sample preservation reagent within the reagent chamber in the sealing cap when the valve assembly is in a closed configuration when the cap is not associated with the sample collection vessel, and the valve assembly being configured to release the sample preservation reagent from the reagent chamber into the sample collection chamber when the sealing cap is associated with the sample collection vessel to put the valve assembly in an open configuration,
the valve assembly including a core, a plurality of fluid vents, and a collar,
the core having a first end adjacent to the reagent chamber, a second end opposite the first end configured to associate with the opening at the top portion of the sample collection vessel, a head member at the first end, and a flange at the second end configured to associate with the upper lip of the sample collection vessel,
the plurality of fluid vents extending through the core in fluid communication with entrance apertures through a side of the head member of the core and exit apertures through the second end of the core, and
the collar being disposed about the core, the collar forming a fluid-tight seal with the head member of the core and obstructing the entrance apertures to retain the sample preservation reagent within the reagent chamber when the valve assembly is in the closed configuration;
placing the biological sample through the opening of the sample collection vessel and into the sample collection chamber; and
associating the sealing cap with the sample collection vessel so that the sealing cap fits over and seals the opening at the top portion of the sample collection vessel to seal the contents of the sample collection chamber,
wherein associating the sealing cap with the sample collection vessel and moving the sealing cap toward the sample collection chamber causes the flange of the core to associate with the upper lip of the sample collection vessel and prevents further movement of the core toward the sample collection chamber, whereupon further movement of the sealing cap toward the sample collection chamber causes translational movement of the collar along a longitudinal axis relative to the head member of the core to put the valve assembly in the open configuration in which the entrance apertures are at least partially unobstructed by the collar such that the sample preservation reagent is permitted to pass from the reagent chamber, through the entrance apertures and fluid vents, out the exit apertures, and into the sample collection chamber to mix with and preserve the biological sample;
the method further comprising:
providing a funnel that is removably attached to the sample collection vessel by a connection mechanism selected from the group consisting of threads, snap fit connections, press fit connections, tongue and groove members, bayonet connections, and interlocking or mechanically coupling mechanisms.

8. The method of claim 7, wherein the funnel has a complementary connection mechanism at a distal end for removeable attachment to the top portion of the sample collection vessel, a sample receiving opening at a proximal end for receiving the biological sample from the user, and an exit opening at the distal end through which the biological sample exits to pass through the opening of sample collection vessel and into the sample collection chamber.

9. The method of claim 1, wherein the sample collection vessel includes a connection member on an exterior surface of the top portion of the sample collection vessel adjacent to the opening, and wherein the sealing cap comprises a complementary connection member located on an inner wall of the sealing cap that is configured to associate with the connection member of the sample collection vessel in order to couple the sealing cap to the sample collection vessel.

10. The method of claim 9, wherein the connection member of the sample collection vessel comprises a ridge projecting away from the sample collection vessel or a depression within the sample collection vessel and the complementary connection member of the sealing cap comprises a hook or ridge sized and shaped to engage the connection member of the sample collection vessel.

11. The method of claim 9, wherein the connection member and the complementary connection member each comprise complementary threads, wherein the complementary threads of the connection member comprise external threads of the sample collection vessel, and wherein the complementary threads of the complementary connection member comprise internal threads of the sealing cap.

12. The method of claim 1, wherein the sample collection vessel includes a generally cylindrical portion having a generally circular cross section of constant diameter extending from the top portion of the sample collection vessel, exclusive of any connection member or mechanism, to a portion of the sample collection vessel defining the sample collection chamber.

13. A method of collecting and preserving a biological sample, the method comprising:
   providing a sample collection kit that comprises
      a sample collection vessel that includes a top portion, an upper lip defining an opening at the top portion, and a sample collection chamber adapted to receive and store a biological sample; and
      a sealing cap that includes a reagent chamber, a valve assembly, and a sample preservation reagent in the reagent chamber,
      the sealing cap being configured to be associated with the sample collection vessel and fit over and seal the opening at the top portion of the sample collection vessel to thereby seal the contents of the sample collection chamber therein,
      the reagent chamber being disposed within the sealing cap, the reagent chamber storing the sample preservation reagent therein, and
      the valve assembly being disposed within the sealing cap, the valve assembly being configured to retain the sample preservation reagent within the reagent chamber in the sealing cap when the valve assembly is in a closed configuration when the cap is not associated with the sample collection vessel, and the valve assembly being configured to release the sample preservation reagent from the reagent chamber into the sample collection chamber when the sealing cap is associated with the sample collection vessel to put the valve assembly in an open configuration,
      the valve assembly including a core, a plurality of fluid vents, and a collar,
         the core having a first end adjacent to the reagent chamber, a second end opposite the first end configured to associate with the opening at the top portion of the sample collection vessel, a head member at the first end, and a flange at the second end configured to associate with the upper lip of the sample collection vessel,
         the plurality of fluid vents extending through the core in fluid communication with entrance apertures through a side of the head member of the core and exit apertures through the second end of the core, and
         the collar being disposed about the core, the collar forming a fluid-tight seal with the head member of the core and obstructing the entrance apertures to retain the sample preservation reagent within the reagent chamber when the valve assembly is in the closed configuration;
   obtaining the biological sample through the opening at the top portion of the sample collection vessel and into the sample collection chamber; and
   associating the sealing cap with the sample collection vessel so that the sealing cap fits over and seals the opening at the top portion of the sample collection vessel to seal the contents of the sample collection chamber,
   wherein associating the sealing cap with the sample collection vessel and moving the sealing cap toward the sample collection chamber causes the flange of the core to associate with the upper lip of the sample collection vessel and prevents further movement of the core toward the sample collection chamber, whereupon further movement of the sealing cap toward the sample collection chamber causes translational movement of the collar along a longitudinal axis relative to the head member of the core to put the valve assembly in the open configuration in which the entrance apertures are at least partially unobstructed by the collar such that the sample preservation reagent is permitted to pass from the reagent chamber, through the entrance apertures and fluid vents, out the exit apertures, and into the sample collection chamber to mix with and preserve the biological sample,
   wherein associating the sealing cap with the sample collection vessel causes a physical rearrangement of the core relative to the collar to put the valve assembly in the open configuration in which the one or more fluid vents are at least partially unobstructed and moved into fluid communication with the reagent chamber, and
   wherein the method further comprises providing a funnel that is removably attachable to the sample collection vessel by a connection mechanism selected from the group consisting of threads, snap fit connections, press fit connections, tongue and groove members, bayonet connections, and interlocking or mechanically coupling mechanisms.

14. The method of claim 13, wherein the funnel has a complementary connection mechanism at a distal end for removeable attachment to the top portion of the sample collection vessel, a sample receiving opening at a proximal end for receiving the biological sample from the user, and an exit opening at the distal end through which the biological sample exits to pass through the opening of sample collection vessel and into the sample collection chamber.

15. The method of claim 13, wherein the sample collection vessel includes a connection member on an exterior surface of the top portion of the sample collection vessel adjacent to the opening, and wherein the sealing cap comprises a complementary connection member located on an inner wall of the sealing cap and that is configured to associate with the connection member of the sample collection vessel in order to couple the sealing cap to the sample collection vessel.

16. A method of collecting and preserving a biological sample, the method comprising:
providing a sample collection vessel that includes a top portion, an upper lip defining an opening at the top portion, and a sample collection chamber adapted to receive and store a biological sample;
providing a sealing cap that includes a reagent chamber, a valve assembly, and a sample preservation reagent in the reagent chamber,
the sealing cap being configured to be associated with the sample collection vessel and fit over and seal the opening at the top portion of the sample collection vessel to thereby seal the contents of the sample collection chamber therein,
the reagent chamber being disposed within the sealing cap, the reagent chamber storing the sample preservation reagent therein, and
the valve assembly being disposed within the sealing cap, the valve assembly being configured to retain the sample preservation reagent within the reagent chamber in the sealing cap when the valve assembly is in a closed configuration when the cap is not associated with the sample collection vessel, and the valve assembly being configured to release the sample preservation reagent from the reagent chamber into the sample collection chamber when the sealing cap is associated with the sample collection vessel to put the valve assembly in an open configuration,
the valve assembly including a core, a plurality of fluid vents, and a collar,
the core having a first end adjacent to the reagent chamber, a second end opposite the first end configured to associate with the opening at the top portion of the sample collection vessel, a head member at the first end, and a flange at the second end configured to associate with the upper lip of the sample collection vessel,
the plurality of fluid vents extending through the core in fluid communication with entrance apertures through a side of the head member of the core and exit apertures through the second end of the core, and
the collar being disposed about the core, the collar forming a fluid-tight seal with the head member of the core and obstructing the entrance apertures to retain the sample preservation reagent within the reagent chamber when the valve assembly is in the closed configuration;
wherein the sealing cap and sample collection are configured such that associating the sealing cap with the sample collection vessel and moving the sealing cap toward the sample collection chamber causes the flange of the core to associate with the upper lip of the sample collection vessel and prevents further movement of the core toward the sample collection chamber, whereupon further movement of the sealing cap toward the sample collection chamber causes translational movement of the collar along a longitudinal axis relative to the head member of the core to put the valve assembly in the open configuration in which the entrance apertures are at least partially unobstructed by the collar such that the sample preservation reagent is permitted to pass from the reagent chamber, through the entrance apertures and fluid vents, out the exit apertures, and into the sample collection chamber to mix with and preserve the biological sample.

17. The method according to claim 16, further comprising providing a funnel that is removably attached to the sample collection vessel, the funnel receiving the biological sample and guiding it through the opening at the top portion of the sample collection vessel and into the sample collection chamber.

18. The method according to claim 17, further comprising removing the funnel from the sample collection vessel to expose the opening at the top portion of the sample collection vessel and associating the sealing cap with the sample collection vessel so that the sealing cap fits over and seals the opening at the top portion of the sample collection vessel to seal the contents of the sample collection chamber.

* * * * *